US006457471B1

(12) United States Patent
Bibi

(10) Patent No.: US 6,457,471 B1
(45) Date of Patent: Oct. 1, 2002

(54) DUAL-PURPOSE MEDICAL DEVICE FOR UPPER AIRWAY TREATMENT AND METHODS FOR USING SAME

(75) Inventor: Noam Bibi, Rehovot (IL)

(73) Assignee: Medihale Ltd., Netanya (IL)

(*) Notice: Subject to any disclaimer, the term of this patent is extended or adjusted under 35 U.S.C. 154(b) by 51 days.

(21) Appl. No.: 09/609,220

(22) Filed: Jun. 30, 2000

(51) Int. Cl.⁷ .............................................. A61M 15/00
(52) U.S. Cl. .............................. 128/203.12; 128/200.24
(58) Field of Search .................. 129/200.11, 200.14, 129/200.21, 200.22, 200.23, 200.24, 203.12, 203.14, 203.19, 203.28, 205.13–205.17; 604/30, 33, 136, 131, 132, 37, 319, 519, 890.1, 151, 152, 259, 94.01, 93.01

(56) References Cited

U.S. PATENT DOCUMENTS

| | | | | |
|---|---|---|---|---|
| 852,828 A | * | 5/1907 | Dorment et al. ............... | 128/29 |
| 1,643,631 A | * | 9/1927 | Schulz .......................... | 128/29 |
| 1,925,230 A | * | 9/1933 | Buckhout .................... | 128/231 |
| 3,106,204 A | * | 10/1963 | Paramelle ..................... | 128/29 |
| 3,626,928 A | * | 12/1971 | Hohokus et al. ............... | 128/2 |
| 3,892,226 A | * | 7/1975 | Rosen ........................... | 128/2 |
| 4,583,972 A | * | 4/1986 | Hunter, III et al. .......... | 604/133 |
| 4,921,488 A | * | 5/1990 | Maitz et al. ................. | 604/153 |
| 4,943,288 A | * | 7/1990 | Kurtz et al. ................. | 604/408 |
| 4,950,247 A | * | 8/1990 | Rosenblatt ................... | 604/181 |
| 5,062,835 A | * | 11/1991 | Maitz et al. ................. | 604/153 |
| 5,078,677 A | * | 1/1992 | Gentelia et al. ............... | 604/4 |
| 5,192,272 A | * | 3/1993 | Faure .......................... | 604/141 |
| 5,201,703 A | * | 4/1993 | Gentelia et al. ............... | 604/4 |
| 5,246,422 A | * | 9/1993 | Favre .......................... | 604/110 |
| 5,318,548 A | * | 6/1994 | Filshie ........................ | 604/319 |
| 5,579,760 A | * | 12/1996 | Kohler ................... | 128/203.15 |
| 5,702,362 A | * | 12/1997 | Herold et al. ................. | 604/58 |
| 5,788,683 A | * | 8/1998 | Martin ........................ | 604/319 |

* cited by examiner

Primary Examiner—Aaron J. Lewis
Assistant Examiner—Teena K Mitchell
(74) Attorney, Agent, or Firm—Mark M. Friedman

(57) ABSTRACT

A dual-purpose medical device for upper airway treatment and methods for using the device are disclosed. The device for upper airway treatment includes two primary components. The first component is a cassette connectable to an airflow generator. The second component is the airflow generator. The airflow generator is manually operable and relies upon ambient air to create a flow of air. The airflow generator is capable of generating airflow through the cassette for either aerosol delivery of a drug or for suction of unwanted secretions. Further disclosed is a method for aerosol delivery of a drug using the disclosed device. The method includes at least two steps. In the first step, the airflow generator is connected to the cassette. In the second step, air is caused to flow through the cassette so that aerosol delivery of a drug in the cassette is accomplished. Further disclosed is a method for suction of unwanted secretions from an airway. The method includes at least two steps. In the first step, the airflow generator is connected to the cassette. In the second step, air is caused to flow through the cassette so that suction of unwanted secretions from an airway is accomplished and so that the unwanted secretions accumulate in the cassette.

17 Claims, 12 Drawing Sheets

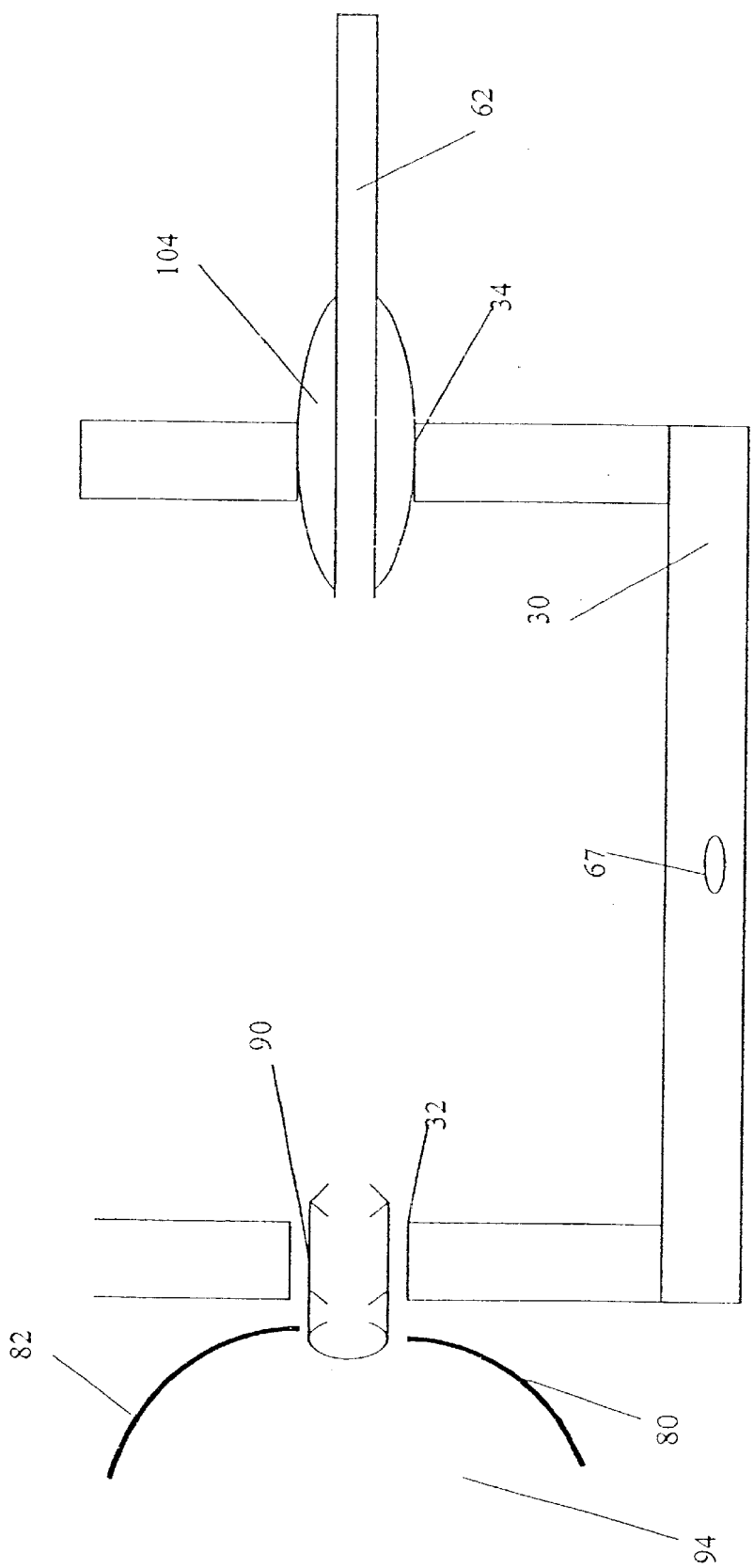

DUAL-PURPOSE MEDICAL DEVICE FOR UPPER AIRWAY TREATMENT AND METHODS FOR USING SAME

FIELD AND BACKGROUND OF THE INVENTION

The present invention relates to a dual-purpose medical device for upper airway treatment and to methods for using the device. More particularly the present invention relates to a manually operated device which is capable of both delivery of drugs and removal of unwanted secretions.

Medical disorders of the upper airway are common. Asthma affects approximately 10% of the adult population. Asthmatic patients, together with those suffering from cystic fibrosis, bronchitis, smoking related disorders and infants with difficulty maintaining adequate oral ventilation are probably found in 20–50% of households. Patients with these disorders are generally treated with drugs delivered as an aerosol suspension, or with suction to remove unwanted secretions, or with both aerosol drugs and suction.

Aerosol delivery of drugs to the airway is typically accomplished by either a stream of air created by a motorized pump, or by use of a pressurized propellant gas (e.g. aerosol canister).

Aerosol delivery devices which include a motorized pump are typically heavy, noisy and expensive. A typical device may cost a consumer in the U.S.A. 70 to 200 dollars. In addition, use of devices of this type often requires measuring and mixing of components of the aerosol. This provides an opportunity for patient error and may lead to delivery of an incorrect dose of medication.

Devices which rely upon a pressurized propellant gas are typically capable of delivering a pre-measured dose of medication with each actuation. However, medication packaged in this way is relatively expensive. In addition, patients with. poor co-ordination (e.g. young children, geriatric patients) often have difficulty using these devices. These patients typically employ a spacing chamber which allows them to draw in medication by inhaling after actuation of the device. Such a spacing chamber typically costs approximately 30 dollars. While devices of this type are often small enough to be easily portable, the spacing chambers employed with these devices are generally large enough that it is inconvenient to carry them.

Suction of unwanted secretions such as mucous from the upper airway (e.g. nose, pharynx) is often performed using devices with electric vacuum pumps. These devices are typically found primarily in hospitals and medical facilities. They are heavy, noisy and expensive. Currently, the primary solution for home suction is a portable device which is the subject of British Pat. No. 2,245,833. This patent does not teach the use of a disposable mucous trap. A re-usable mucous trap is a potential source of infection and represents a serious dis-advantage to practice of the teachings of this patent.

There is thus a widely recognized need for, and it would be highly advantageous to have, medical device for upper airway treatment devoid of the above limitation. Ideally, such a device would be a dual-purpose device capable of performing both aerosol delivery and suction treatments.

SUMMARY OF THE INVENTION

According to one aspect of the present invention there is provided a dual-purpose medical device for upper airway treatment, the device comprising: (a) a disposable cassette having a first opening, a second opening and an interior volume, the cassette being connectable to an airflow generator by means of the first opening; (b) the airflow generator; wherein the airflow generator is manually operable and relies upon ambient air to create a flow of air; and wherein the airflow generator is capable of generating a flow of air through the disposable cassette in at least two directions, such that: (i) aerosol delivery of a drug residing in the internal volume of the cassette may be accomplished if the flow of air is in a first direction into the internal volume of the cassette via the first opening and outward from the internal volume via the second opening towards an airway of a patient; and (ii) suction of unwanted secretions may be accomplished if the flow of air is in a second direction into the internal volume of the cassette via the second opening and outward from the internal volume via the first opening towards the airflow generator.

According to another aspect of the present invention there is provided a method for aerosol delivery of a drug, the method comprising the steps of: (a) connecting an airflow generator to a disposable cassette via a first opening of the cassette, the cassette comprising the first opening, a second opening and an interior volume; and (b) causing air to flow into the internal volume of the cassette via the first opening and outward from the internal volume via the second opening towards an airway of a patient such that the aerosol delivery of a drug residing in the internal volume of the cassette is accomplished; wherein the airflow generator is manually operable and relies upon ambient air to create a flow of air.

According to yet another aspect of the present invention there is provided a method for suction of unwanted secretions from an airway, the method comprising the steps of: (a) connecting an airflow generator to a disposable cassette via a first opening of the cassette, the cassette comprising the first opening, a second opening and an interior volume; and (b) causing air to flow into the internal volume of the cassette via the second opening and outward from the internal volume via the first opening towards the airflow generator such that the suction of unwanted secretions from an airway is accomplished and such that the unwanted secretions accumulate in the cassette; wherein the airflow generator is manually operable and relies upon ambient air to create a flow of air.

According to further features in preferred embodiments of the invention described below, the device further comprises (c) a re-usable holder for the cassette.

According to still further features in the described preferred embodiments the cassette further comprises: (i) at least one partition dividing the interior volume into at least two chambers; and (ii) an openable region in each of the at least one partition.

According to still further features in the described preferred embodiments the device further comprising perforations surrounding at least a portion of the openable region in each of the at least one partition such that opening thereof is facilitated by the perforations.

According to still further features in the described preferred embodiments the device further comprises (c) a mechanism for opening the openable region.

According to still further features in the described preferred embodiments the airflow generator is a compressible elastic container.

According to still further features in the described preferred embodiments compression of the compressible elastic container may cause the flow of air to be in the first direction and subsequent expansion of the compressible elastic container may cause the flow of air to be in the second direction.

According to still further features in the described preferred embodiments the device further comprises at least one element selected from the group consisting of: (i) an aerosol jet connectable to the second opening of the cassette and capable of delivering the drug as a plurality of microdroplets; (ii) a suction tube connectable to the second opening of the cassette and insertable into a bodily orifice of a patient.

According to still further features in the described preferred embodiments the method comprises the additional step of: (c) placing the cassette within a re-usable holder.

According to still further features in the described preferred embodiments the method comprises the additional step of (c) providing within the cassette: (i) at least one partition dividing the interior volume into at least two chambers; and (ii) an openable region in each of the at least one partition wherein at least one of the chambers contains at least one component of the drug.

According to still further features in the described preferred embodiments the method comprises the additional step of providing perforations surrounding a portion of the openable region in each of the at least one partition such that opening thereof is facilitated by the perforations.

According to still further features in the described preferred embodiments the method comprises the additional step of opening the openable region by means of mechanism for opening the openable region.

According to still further features in the described preferred embodiments the method comprises the additional step of aerosolizing the drug to form a plurality of microdroplets by means of an aerosol jet connected to the second opening of the cassette.

According to still further features in the described preferred embodiments the airflow generator is a compressible elastic container such that the step of causing air to flow into the internal volume of the cassette is effected by compression of the compressible elastic container.

According to still further features in the described preferred embodiments the method comprises the additional step of drawing unwanted secretions through a suction tube connected to the second opening of the cassette and inserted into a bodily orifice of a patient.

The present invention successfully addresses the shortcomings of the presently known configurations by providing a dual-purpose medical device for upper airway treatment and methods for using same, which facilitates both aerosol delivery of a drug and hygienic removal of unwanted secretions.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 1 is a side view of an airflow generator according to the present invention;

FIG. 2 is a side view of the airflow generator of FIG. 1 in a collapsed state;

FIG. 3 is a transparent view of a disposable cassette according to the present invention;

FIG. 4 shows insertion of a disposable cassette of the present invention in a re-usable holder according to the present invention;

FIGS. 5*a* and 5*b* depict opening of an openable region according to the present invention;

FIGS. 6*a* and 6*b* depict opening of an openable region according to an alternate preferred embodiment of the present invention;

FIGS. 7*a*, 7*b*, and 7*c* show details of one preferred embodiment of an openable region and a mechanism for opening same according to the present invention;

FIG. 8 is schematic diagram of a device according to the present invention configured for aerosol delivery of a drug;

FIG. 9 is a cut away view of a suction tube according to the present invention;

FIG. 10 is a side view of a device according to the present invention configured for suction of unwanted secretions from an airway;

DESCRIPTION OF THE PREFERRED EMBODIMENTS

The present invention is of a dual-purpose medical device for upper airway treatment and of methods for using the device which can be manually operated. Specifically, the present invention can be used to both deliver a drug by aerosol and to remove unwanted secretions hygienically.

The principles and operation of a dual-purpose medical device for upper airway treatment and of methods for using the device according to the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

For purposes of this specification and the accompanying claims, the term "drug" refers to any material which is delivered for purposes of therapy. Intended therapy may work by, for example, a physiologic mechanism or a simple physical effect. The term drug therefore specifically includes, but is not limited to, water, saline solutions, vasoconstrictors, antihistamines, steroid compounds, decongestants, aroma-therapy agents, plant extracts, oils, anti-inflammatory compounds and antibiotics as well as any combination thereof. A drug may take many physical forms, including but not limited to, a liquid, a powder, a gel, an emulsion, a gas, and a solid. It will be appreciated that those solids which have a high vapor pressure at room temperature, i.e. those which tend to sublime, are more suited for use as a drug in the context of the present invention than those solids with a low vapor pressure at room temperature.

For purposes of this specification and the accompanying claims, the term "patient" refers to any person or animal using the device of, or practicing a method of, the present invention.

Referring now to the drawings, a narrative description of the component parts of a device 20 for upper airway treatment, and their workings, will be presented.

Figure 1:
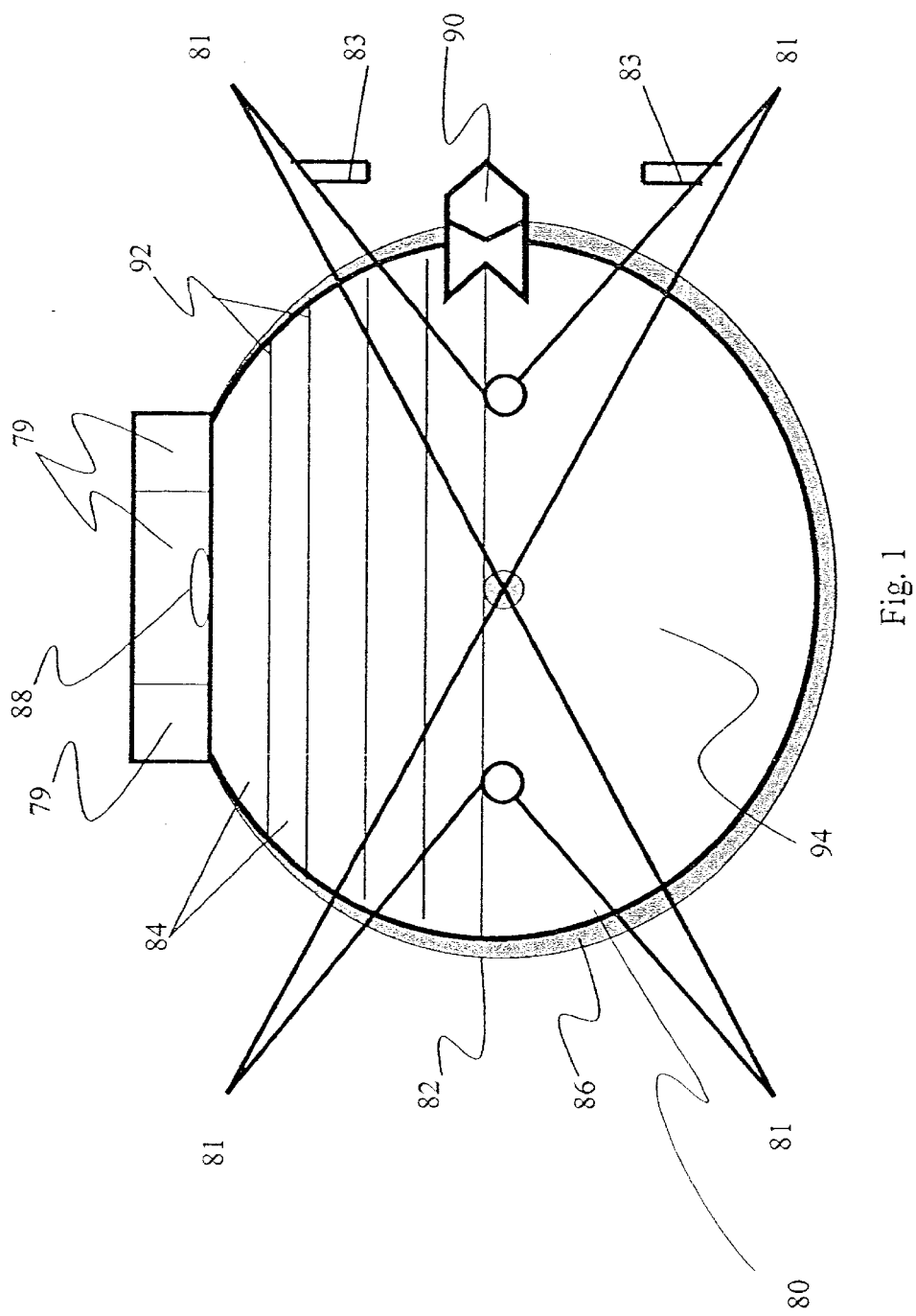
Figure 2:
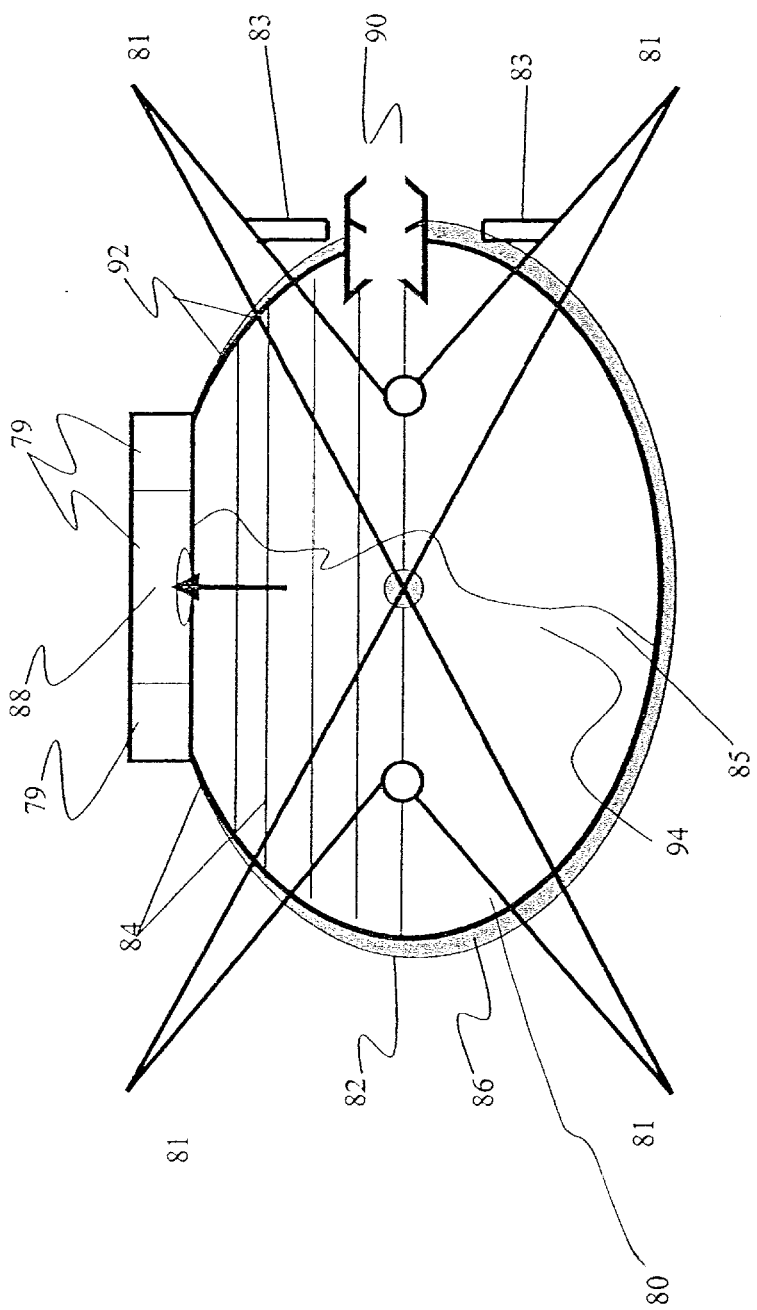
Figure 3:
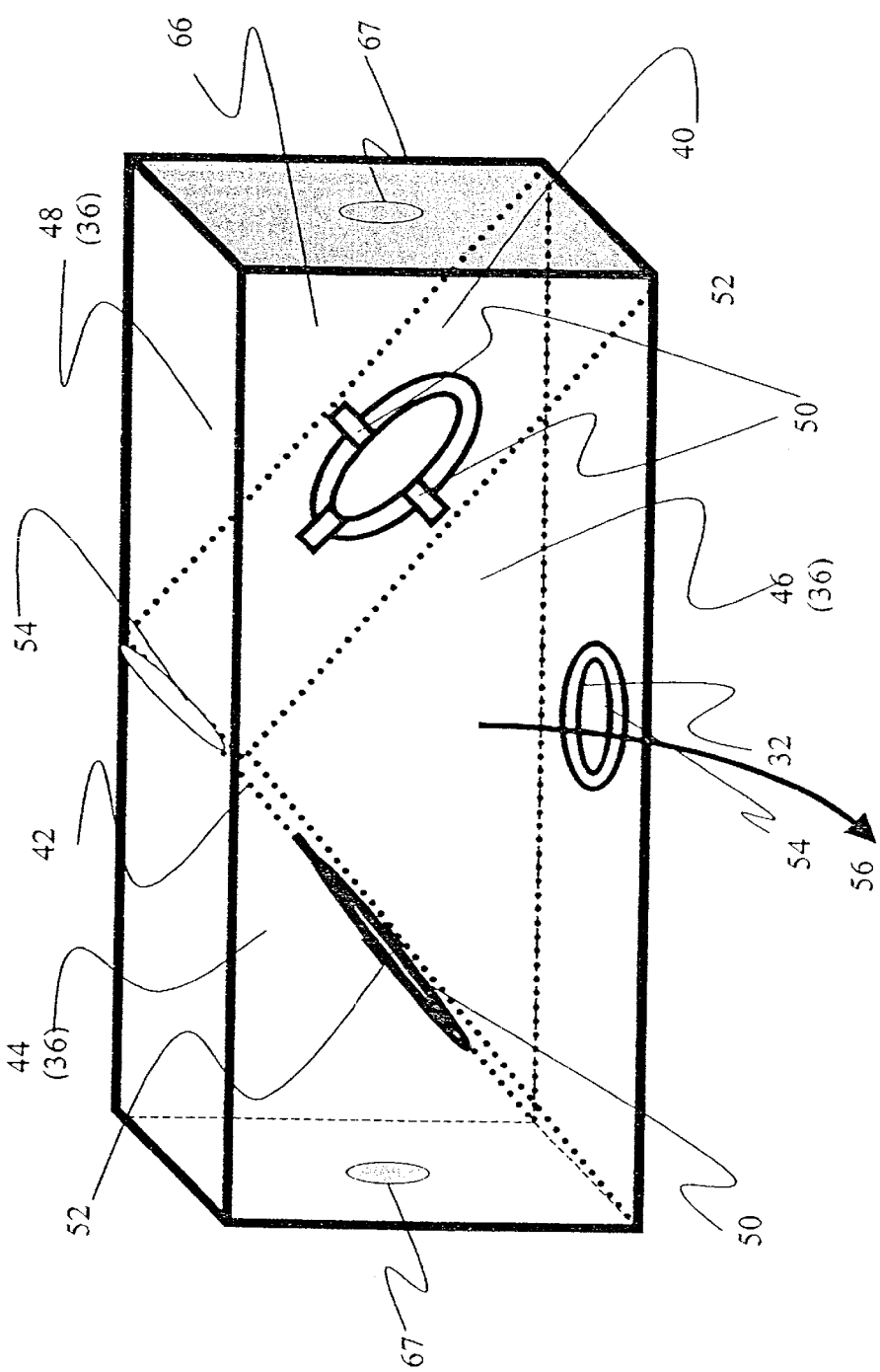
Figure 4:
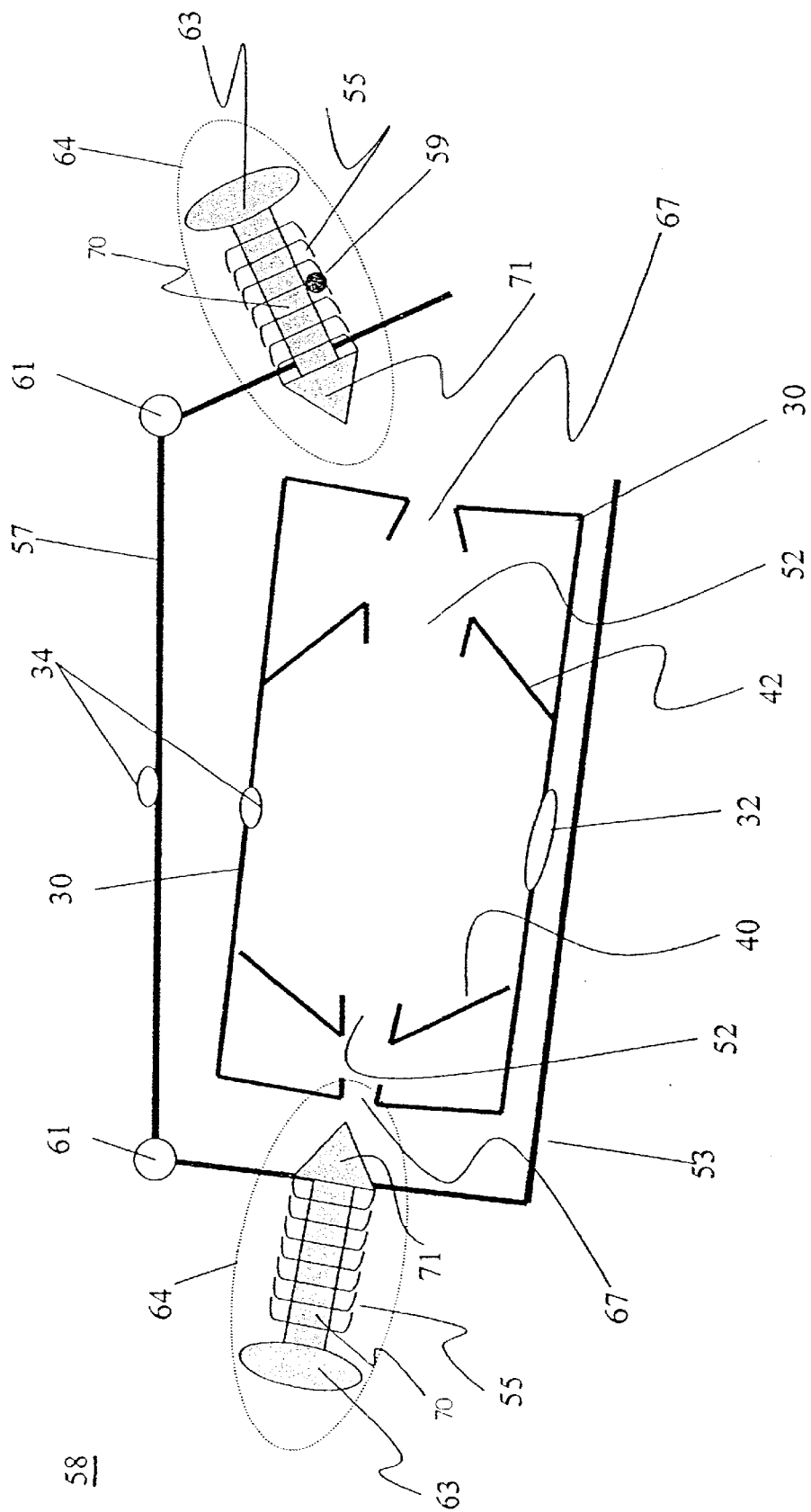
Figure 8:
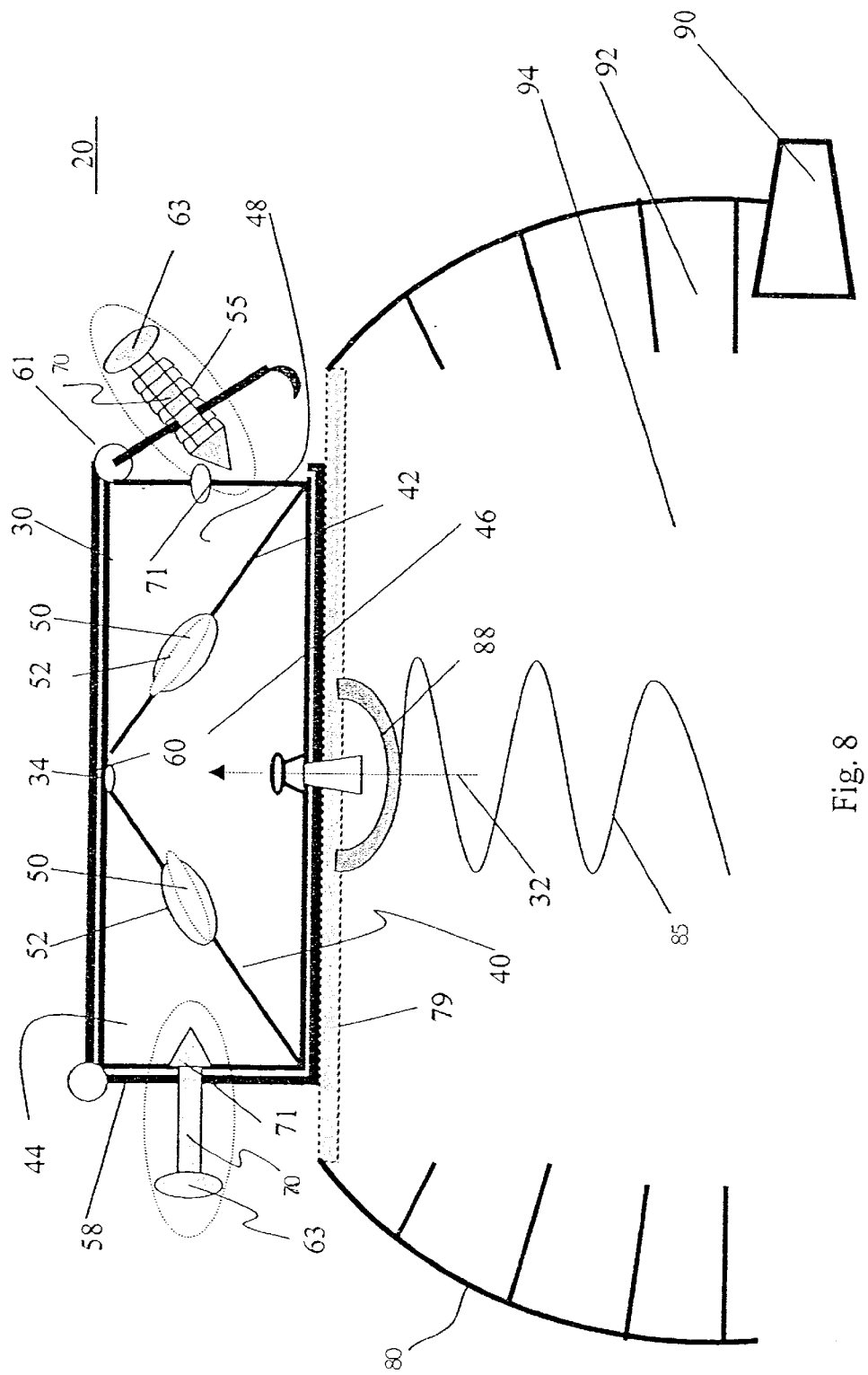

Device 20 for upper airway treatment (FIG. 8) includes a disposable cassette 30 (FIG. 3) having a first opening 32 or 67, a second opening 34 or 67 and an interior volume 36. In some cases, one first and second opening may be used for aerosol delivery of a drug (e.g. 32 and 34) and a second first and second opening may be used for suction of unwanted secretions from an airway (e.g. pair of 67). Cassette 30 typically is supplied as a sealed unit containing a pre-measured dose of a drug. In order to reduce risk of infection during use, cassette 30 is often supplied in a sterile wrapper which serves also to seal holes 32, 34, and 67 prior to use. This insures that the premeasured dose of drug will remain in cassette 30. Alternately or additionally, each of holes 32, 34, and 67 may be sealed with an openable region and perforations as described hereinbelow for partitions 40 and 42. Alternately or additionally, mechanism 64 for opening may seal one or more of holes 32, 34, and 67. Alternately or additionally, mechanism 64 for opening may be employed to break a seal on one or more of holes 32, 34, and 67. Alternately or additionally, valves 88 or 90 may be employed to break a seal on one or more of holes 32, 34, and 67 as cassette 30 is connected to airflow generator 80.

Cassette 30 is connectable to an airflow generator 80 (FIGS. 1, 2, 8 and 10) by means of first opening 32 or 67. Airflow generator 80 is manually operable and relies upon ambient air to create a flow of air. Compression of a compressible elastic container 82 causes the flow 54 of air to be in a first direction, outwards via outlet valve 88. When cassette 30 is attached to airflow generator 80 during compression, this causes airflow 54 into interior volume 36 of cassette 30 via first opening (e.g. 32, as pictured in FIG. 3) allowing aerosl delivery of a drug from second opening 34.

Subsequent expansion of compressible elastic container 82 causes the flow 56 of air to be in a second direction, inwards via intake valve 90. If cassette 30 is connected to valve 90 during this expansion, airflow will be in a second direction 56, facilitating suction of unwanted secretions from an airway. Although pictured as separate valves, valves 88 and 90 may be a single variable direction valve according to some embodiments of the invention. According to some preferred embodiments, valve 90 takes in air only when external pressure is applied, for example by a finger or by spring holders 83. According to preferred embodiments of the present invention, airflow generator 80 may include a flattened cassette-accommodating portion 79. According to additional preferred embodiments of the present invention, airflow generator 80 may be equipped with one or more springs 85. These may be either externally mounted on mounting arms 81 containing spring holders 83 or inside elastic container 82. Compressible elastic container 82 may be divided into an elastic portion 84 and an inelastic portion 86. Elastic portion 84 may be strengthened by rigid rings 92.

When airflow generator 80 is connected to disposable cassette 30, it is capable of generating a flow of air through disposable cassette 30 in at least two directions. This means that aerosol delivery of a drug residing in internal volume 36 of cassette 30 may be accomplished if the flow of air is in a first direction into internal volume 36 of cassette 30 via a first opening (e.g. 32) and outward from the internal volume via a second opening (e.g. 34) towards an airway of a patient. Further, suction of unwanted secretions may be accomplished if the flow of air is in a second direction into internal volume 36 of cassette 30 via a first opening (for example 32, 34 or 67) and outward from internal volume 36 via a second opening (for example 32, 34 or 67) towards the airflow generator. Open holes (for example 32, 34 or 67) may be covered, for example by a finger, during use of device 20 for suction.

According to some preferred embodiments, device 20 further includes a re-usable holder 58 (FIGS. 4, 5a, 5b, 6a and 6b) for cassette 30. Holder 58 may be supplied either as a separate unit, or constructed as an integral portion of airflow generator 80, or supplied with cassette 30 inside. Holder 58 has fixed sides 53 and may have an openable top 57, at least one openable side 59, or both. Openable top 57 and side 59 may be equipped with, for example, hinges 61 in order to facilitate opening of holder 58.

Figure 7A:
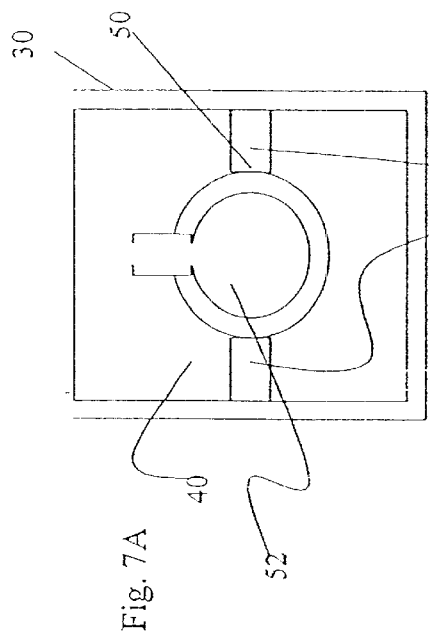

According to some preferred embodiments, cassette 30 may further include at least one partition (two are pictured 40 and 42) dividing interior volume 36 into at least two chambers (three are pictured 44, 46 and 48). Each partition (40 and 42) includes therein an openable region 52 (FIGS. 7a and 7b). Perforations 50 may surround at least a portion of each openable region 52 in partition (40 and 42) such that opening thereof is facilitated by perforations 50. In some cases, a mechanism for opening 64 openable region 40 and 42 is further provided. In other cases, increased airpressure in cassette 30 may be used to open openable region 52.

Figure 5A:
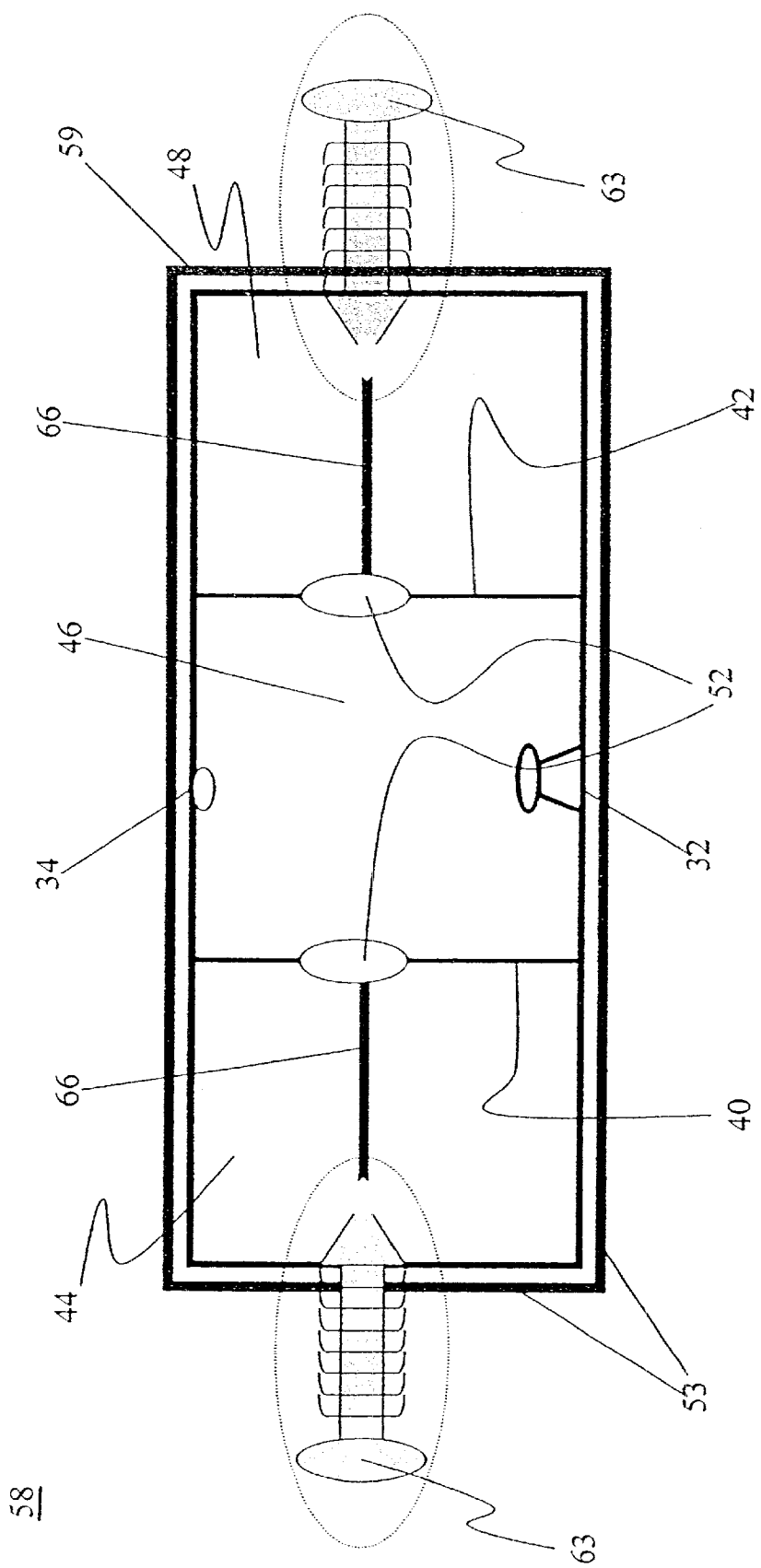
Figure 5B:
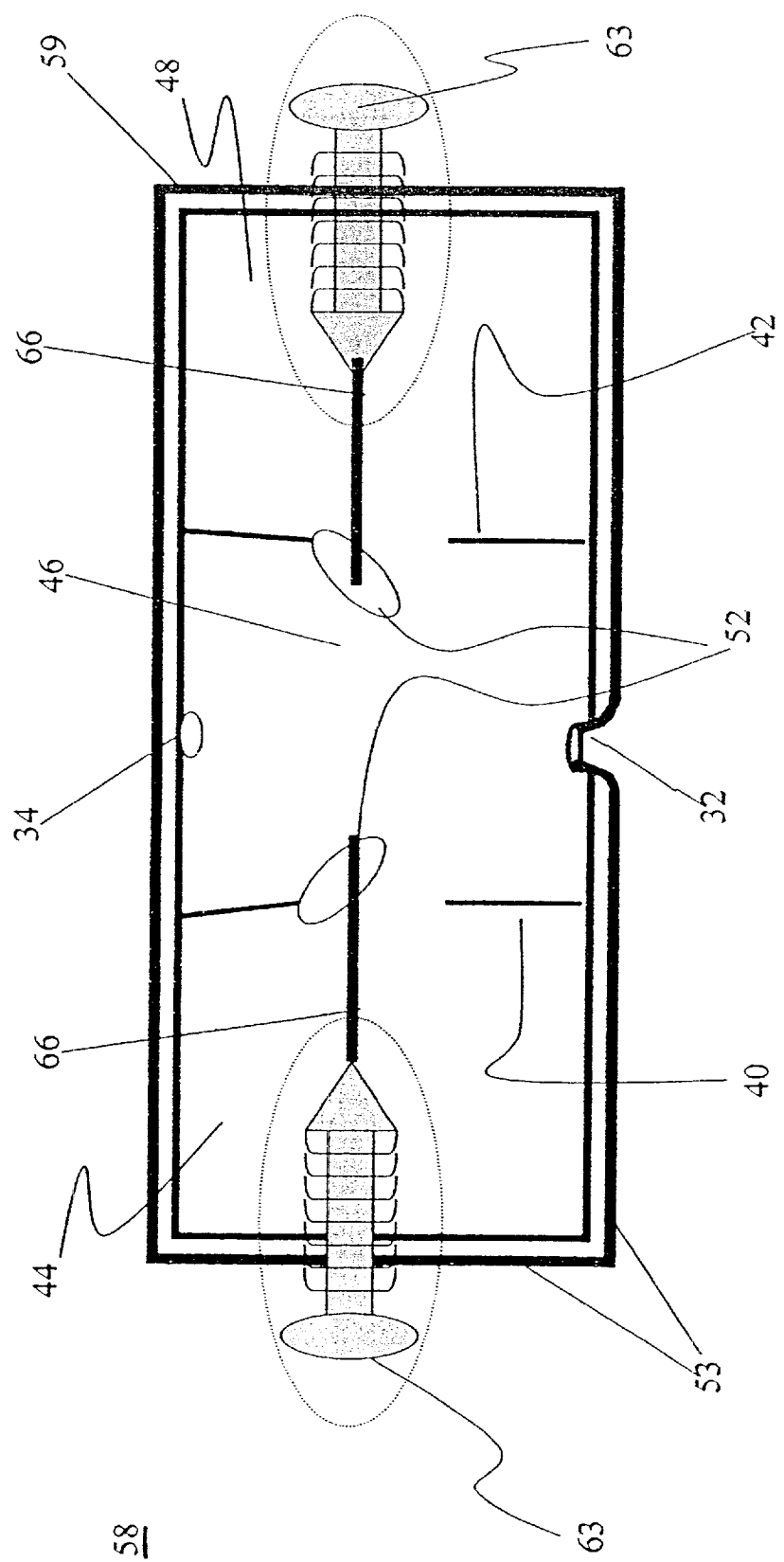
Figure 6A:
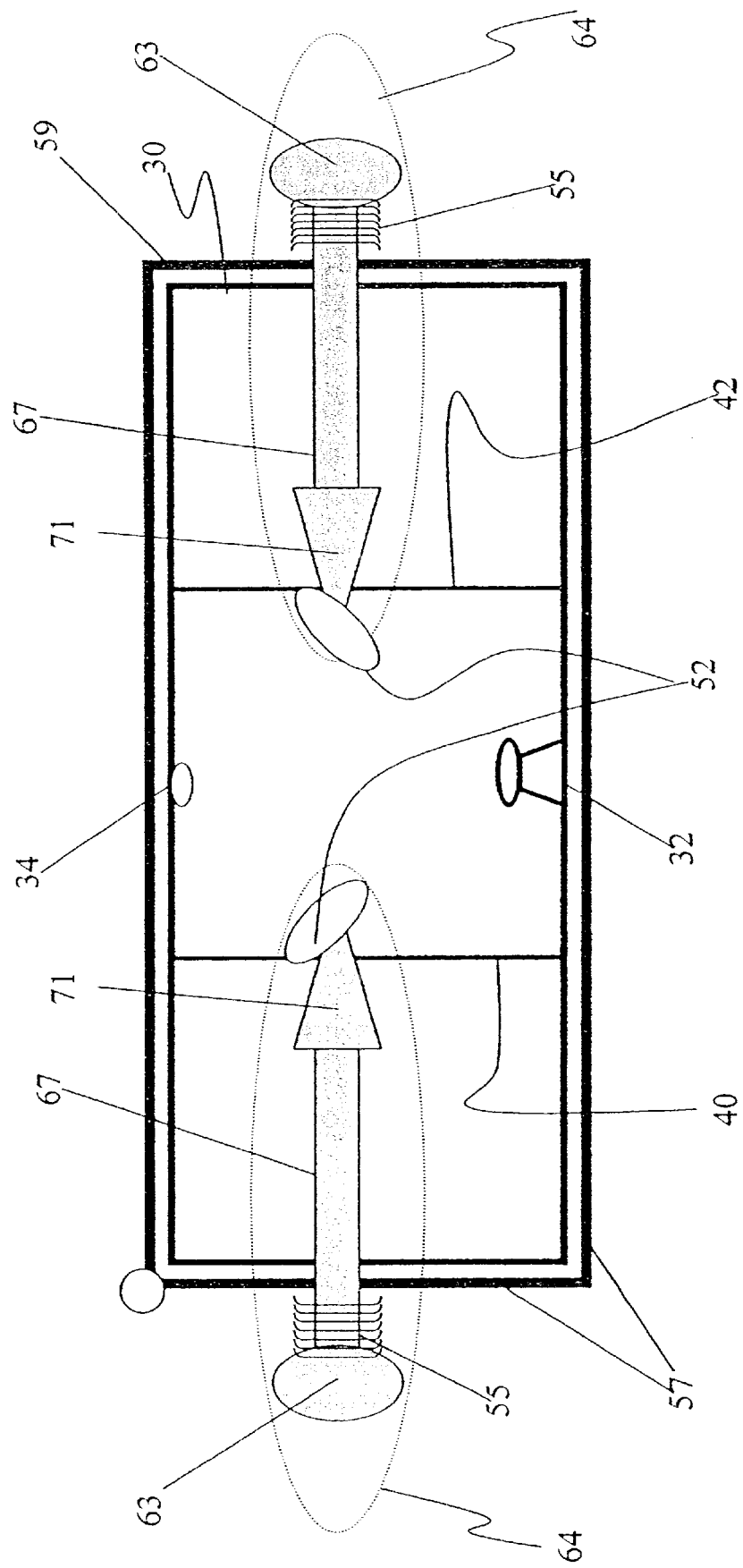
Figure 6B:
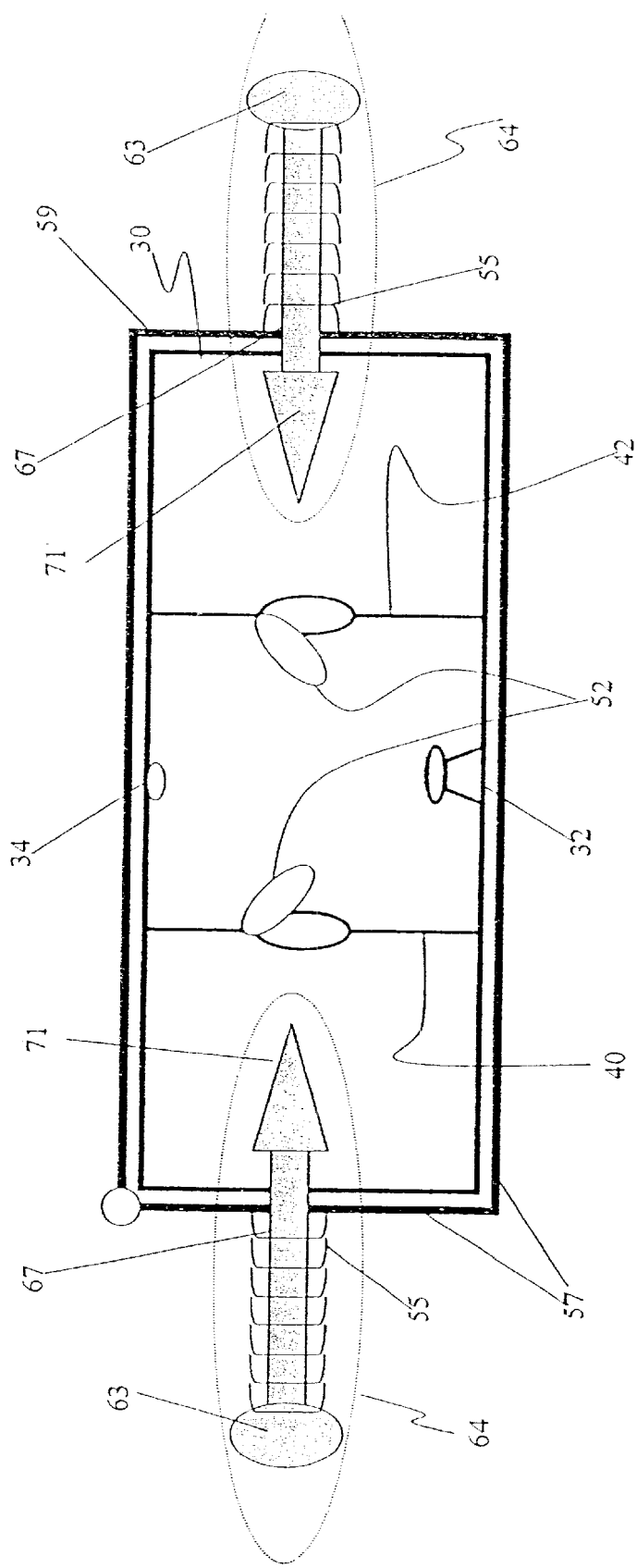
Figure 7C:
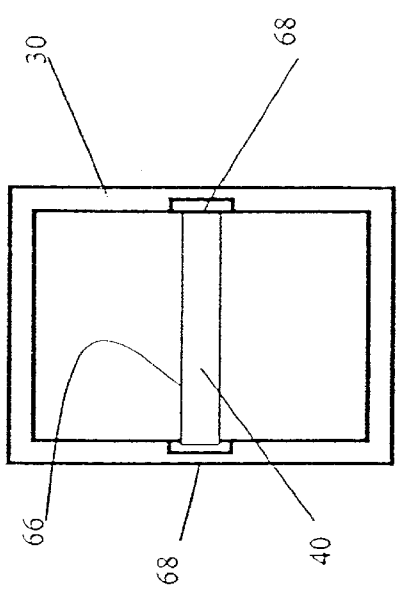
Figure 7B:
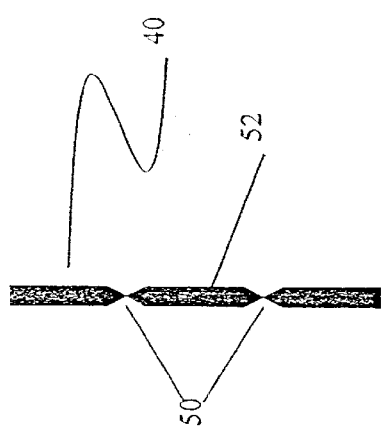

Mechanism for opening 64 may include, for example, (FIG. 7c) a moveable plate 66 capable of translational motion along rails 68 within interior 36 of cassette 30 (FIG. 7c). As shown in FIGS. 5a and 5b, translational motion of moveable plate 66, for example by pressing on a widened end 63 of a piston protruding from holder 58, causes openable region 52 to be opened by breaking perforations 50. This creates channels of fluid communication between chambers 44, 46, and 48 of interior 36 of cassette 30. This fluid communication may facilitate, for example, mixing of components of a drug to be delivered via aerosol as air flows through interior 36.

Alternately, or additionally, mechanism for opening 64 (dashed oval) may include (FIGS. 4, 6a and 6b), for example, pistons 72 having widened ends 63 and being moveable against spring tension of springs 55. Pistons 72 move within holes 67 ends thereof 71 are capable of contacting openable regions 52 and opening them by braking perforations 50.

Device 20 may further include additional features, including but not limited to, an aerosol jet 60 (FIG. 8) connectable to second opening 34 of cassette 30. Aerosol jet 60 is capable of delivering the drug as a plurality of micro-droplets. Aerosol jet 60 may discharge into a spacer, such as an aerosl cloud enhancer and face mask (e.g. one produced by DHD Health Care Corporation, Canastota, NY, USA or DEY, Napa, Calif., USA), or to any tube used for endoscopy (e.g. bronchoscope, gastroscope).

Figure 9:
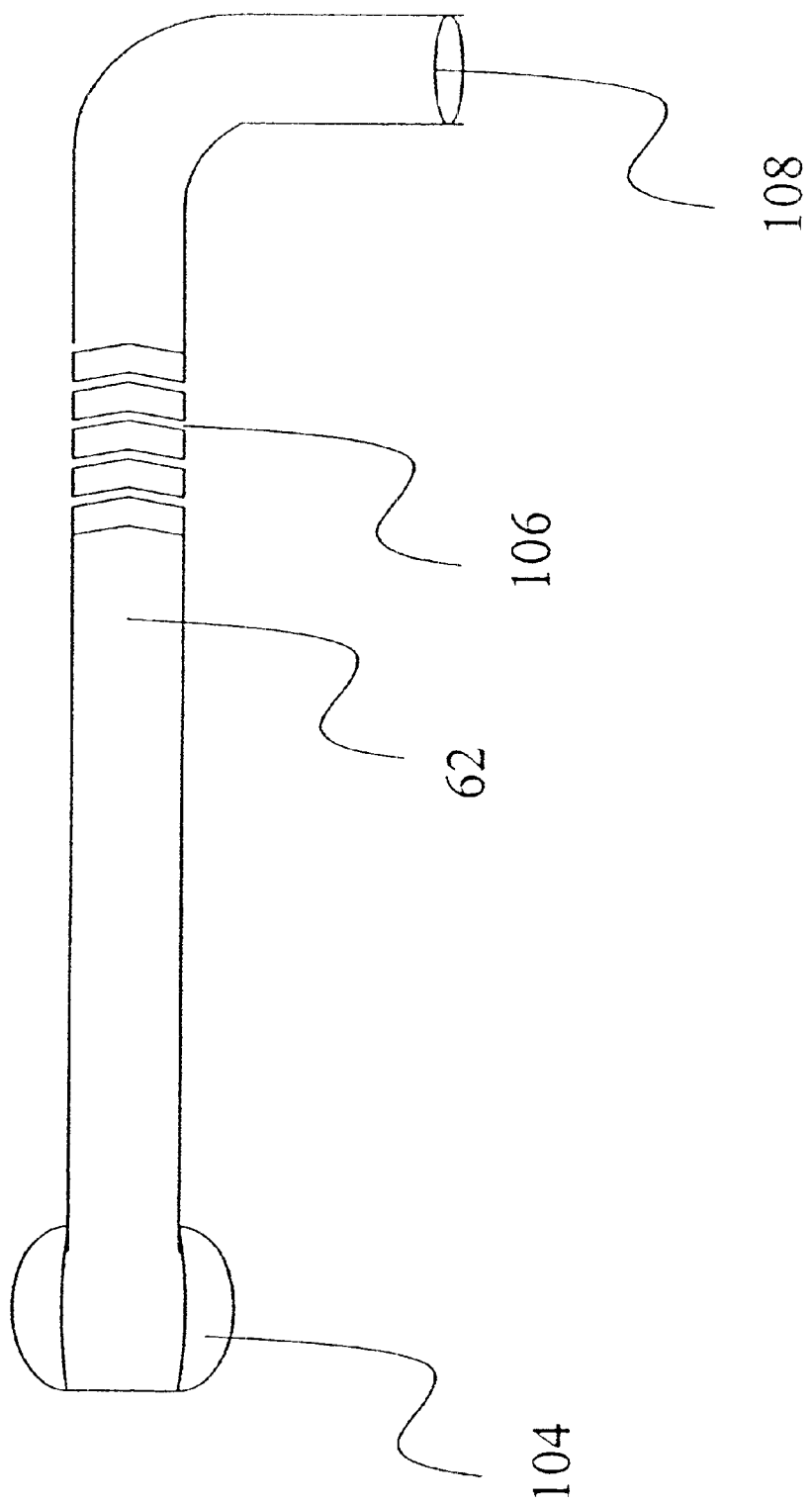

Device 20 may further include additional features, including but not limited to, a suction tube 62 (FIGS. 9 and 10) connectable to an opening (for example 32, 34 or 67) of cassette 30 via widened end 104 and insertable into a bodily orifice of a patient for removal of unwanted secretions therefrom via end 108.

The present invention is further embodied by a method for aerosol delivery of a drug. The method includes at least two steps. The first step includes connecting airflow generator 80 to disposable cassette 30 via first opening 32 of cassette 30. Cassette 30 includes first opening 32, second opening 34 and interior volume 36. The second step includes causing air to flow into internal volume 36 of cassette 30 via first opening 32 and outward from internal volume 36 via second opening 34 towards an airway of a patient. In this way, aerosol delivery of a drug residing in internal volume 36 of cassette 30 is accomplished. Airflow generator 80 is manually operable and relies upon ambient air to create a flow of air. Airflow generator 80 can be, for example, a compressible elastic container 82 (as described hereinabove) such that the step of causing air to flow into internal volume 36 of cassette 30 is effected by compression of elastic container 82. According to some preferred embodiments, the method includes the additional step of placing cassette 30 within a re-usable holder 58.

According to some preferred embodiments, the method includes an additional step of providing additional items associated with cassette 30. These items may include, but are not limited to, at least one partition (40 or 42) dividing interior volume 36 into at least two chambers (44, 46, and 48) and an openable region 52 in each of partitions (40 or 42). At least one of the chambers (44, 46, and 48) contains at least one component of the drug. Alternately, the drug may have several components, each component being stored separately in chambers 44, 46, and 48 and mixed after opening of openable regions 52 in partitions 40 and 42. In some cases, perforations 50 surrounding a portion of openable region 52 in each partition (40 or 42) such that opening thereof is facilitated by perforations 50. In some cases the method further includes an additional step which includes opening openable region 52 by means of mechanism for opening 64 openable region 52 as described hereinabove.

According to some preferred embodiments, the method includes the additional step of aerosolizing the drug to form a plurality of micro-droplets. This step may be accomplished, for example, by means of an aerosol jet 60 connected to second opening 34 of cassette 30. Aerosol jet 60 may be one of many commercially available devices, for example a microsprayer™ (PennCentury, Inc., Philadelphia, Pa., USA).

The invention is further embodied by a method for suction of unwanted secretions from an airway. The method includes two steps. The first step includes connecting airflow generator 80 (as described hereinabove) to disposable cassette 30 (as described hereinabove) via a first opening (for example 32, 34 or 67) of cassette 30. The second step includes causing air to flow into internal volume 36 of cassette 30 via a second opening (for example 32, 34 or 67) and outward from internal volume 36 via first opening (for example 32, 34 or 67) towards airflow generator 80. In this way, the suction of unwanted secretions from an airway is accomplished and the unwanted secretions accumulate in cassette 30. According to preferred embodiments of the present invention, airflow generator 80 is manually operable and relies upon ambient air to create a flow of air.

According to preferred embodiments of the invention, the method includes an additional step which includes drawing unwanted secretions through a suction tube 62 (described hereinabove) connected to a second opening (for example 32, 34 or 67) of cassette 30 and inserted into a bodily orifice of a patient. A bodily orifice might be, for example, a nostril, a mouth or a throat.

Dimensions of cassette 30 are preferably within the following ranges although other sizes are within the scope of the invention:

Height:
   0.5 to 3 cm, more preferably 0.7 to 2 cm, most preferably approximately 1 cm.

Width:
   0.5 to 3 cm, more preferably 0.7 to 2 cm, most preferably approximately 1 cm.

Length:
   0.5 to 7 cm, more preferably 1 to 5 cm, most preferably approximately 3 cm.

The volume of air delivered by a single compression of elastic container 82 is preferably in the range of 0.5 to 100 ml, more preferably 1 to 20 ml, still more preferably 2 to 4 ml, most preferably approximately 2.5 ml although other volumes are within the scope of the invention. It will be appreciated that similar volumes will be vacuumed into cassette 30 during practice of the disclosed method for suction of unwanted secretions from an airway.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A dual-purpose medical device for upper airway treatment, the device comprising:
   (a) a disposable cassette having a first opening, a second opening and an interior volume, said cassette being connectable to an airflow generator by means of said first opening said cassette further comprising:
      (i) at least one partition dividing said interior volume into at least two chambers; and
      (ii) an irreversibly openable region in each of said at least one partition;
   (b) said airflow generator having an intake valve;
   wherein said airflow generator is manually operable and relies upon ambient air to create a flow of air; and
   wherein said airflow generator is capable of generating a flow of air through said disposable cassette in at least two directions, such that:
      (i) aerosol delivery of a drug residing in said internal volume of said cassette may be accomplished if said flow of air is in a first direction into said internal volume of said cassette via said first opening and outward from said internal volume via said second opening towards an airway of a patient; and
      (ii) suction of unwanted secretions may be accomplished if said flow of air is in a second direction into said internal volume of said cassette via said second opening and outward from said internal volume via said first opening towards said airflow generator.

2. The device of claim 1, further comprising:
   (c) a re-usable holder for said cassette.

3. The device of claim 1, further comprising perforations surrounding at least a portion of said openable region in each of said at least one partition such that opening thereof is facilitated by said perforations.

4. The device of claim 1, further comprising:

(c) a mechanism for opening said openable region.

5. The device of claim 1, wherein said airflow generator is a compressible elastic container.

6. The device of claim 5, wherein compression of said compressible elastic container may cause said flow of air to be in said first direction and subsequent expansion of said compressible elastic container may cause said flow of air to be in said second direction.

7. The device of claim 1, further comprising at least one element selected from the group consisting of:

(i) an aerosol jet connectable to said second opening of said cassette and capable of delivering said drug as a plurality of micro-droplets;

(ii) a suction tube connectable to said second opening of said cassette and insertable into a bodily orifice of a patient.

8. A method for aerosol delivery of a drug, the method comprising the steps of:

(a) connecting an airflow generator having an intake valve to a disposable cassette via a first opening of said cassette, said cassette comprising said first opening, a second opening and an interior volume, and i) at least one partition dividing said interior volume into at least two chambers; and (ii) an irreversibly openable region in each of said at least one partition; and (b) causing air to flow into said internal volume of said cassette via said first opening and outward from said internal volume via said second opening towards an airway of a patient such that the aerosol delivery of a drug residing in said internal volume of said cassette is accomplished;

wherein said airflow generator is manually operable and relies upon ambient air to create a flow of air.

9. The method of claim 8, comprising the additional step of:

(c) placing said cassette within a re-usable holder.

10. The method of claim 8, comprising the additional step of providing perforations surrounding a portion of said openable region in each of said at least one partition such that opening thereof is facilitated by said perforations.

11. The method of claim 9, comprising the additional step of opening said openable region by means of mechanism for opening said openable region.

12. The method of claim 8, wherein said airflow generator is a compressible elastic container such that said step of causing air to flow into said internal volume of said cassette is effected by compression of said compressible elastic container.

13. The method of claim 8, comprising the additional step of aerosolizing said drug to form a plurality of micro-droplets by means of an aerosol jet connected to said second opening of said cassette.

14. A method for suction of unwanted secretions from an airway, the method comprising the steps of:

(a) connecting an airflow generator having an intake valve to a disposable cassette via a first opening of said cassette, said cassette comprising said first opening, a second opening and an interior volume; and (b) causing air to flow into said internal volume of said cassette via said second opening and outward from said internal volume via said first opening towards said airflow generator such that the suction of unwanted secretions from an airway is accomplished and such that said unwanted secretions accumulate in said cassette;

wherein said airflow generator is manually operable and relies upon ambient air to create a flow of air.

15. The method of claim 14, comprising the additional step of:

(c) placing said cassette within a re-usable holder.

16. The method of claim 14, wherein said airflow generator is a compressible elastic container such that said step of causing air to flow into said internal volume of said cassette is affected by compression of said compressible elastic container.

17. The method of claim 14, comprising the additional step of drawing unwanted secretions through a suction tube connected to said second opening of said cassette and inserted into a bodily orifice of a patient.

* * * * *

UNITED STATES PATENT AND TRADEMARK OFFICE
CERTIFICATE OF CORRECTION

PATENT NO.    : 6,457,471 B1
DATED         : October 1, 2002
INVENTOR(S)   : Bibi It is certified that error appears in the above-identified patent and that said Letters Patent is hereby corrected as shown below:

Column 9,
Lines 51, 52, 53, 54 and 55, "said internal volume" should be shown as -- said interior volume --
Lines 28, 30 and 32, "said internal volume" should be shown as -- said interior volume --

Column 10,
Lines 19 and 21, "said internal volume" should be shown as -- said interior volume --

Signed and Sealed this

First Day of April, 2003

JAMES E. ROGAN
*Director of the United States Patent and Trademark Office*

UNITED STATES PATENT AND TRADEMARK OFFICE
CERTIFICATE OF CORRECTION

PATENT NO.    : 6,457,471 B1
DATED         : October 1, 2002
INVENTOR(S)   : Bibi It is certified that error appears in the above-identified patent and that said Letters Patent is hereby corrected as shown below:

<u>Column 8,</u>
Lines 51, 52, 53, 54 and 55, "said internal volume" should be shown as -- said interior volume --

<u>Column 9,</u>
Lines 28, 30 and 32, "said internal volume" should be shown as -- said interior volume --

<u>Column 10,</u>
Lines 19 and 21, "said internal volume" should be shown as -- said interior volume --

This certificate supersedes Certificate of Correction issued April 1, 2003.

Signed and Sealed this

Fifteenth Day of July, 2003

JAMES E. ROGAN
*Director of the United States Patent and Trademark Office*